United States Patent
Wieland et al.

(10) Patent No.: US 10,076,483 B2
(45) Date of Patent: Sep. 18, 2018

(54) STEROID CARBOXYLIC ACID ESTERS, COMPOSITIONS CONTAINING STEROID CARBOXYLIC ACID ESTERS, AND USE OF SAID COMPOSITIONS IN LOCAL TOPICAL APPLICATIONS FOR COSMETIC OR DERMATOLOGICAL PURPOSES

(71) Applicant: CHelac Holding GmbH, Freiburg (DE)

(72) Inventors: Heinrich Wieland, St. Peter (DE); Marc A. Kessemeier, Emmendingen (DE); Ralf Zuhse, Berlin (DE)

(73) Assignee: Chelac Holding GmbH, Freiburg (DE)

(*) Notice: Subject to any disclaimer, the term of this patent is extended or adjusted under 35 U.S.C. 154(b) by 0 days.

(21) Appl. No.: 15/028,768

(22) PCT Filed: Oct. 15, 2014

(86) PCT No.: PCT/DE2014/100366
§ 371 (c)(1),
(2) Date: Apr. 12, 2016

(87) PCT Pub. No.: WO2015/055179
PCT Pub. Date: Apr. 23, 2015

(65) Prior Publication Data
US 2016/0235644 A1 Aug. 18, 2016

(30) Foreign Application Priority Data

Oct. 15, 2013 (DE) .................. 10 2013 111 391

(51) Int. Cl.
| | | |
|---|---|---|
| A61K 31/566 | (2006.01) | |
| A61K 8/63 | (2006.01) | |
| A61Q 19/00 | (2006.01) | |
| A61Q 19/06 | (2006.01) | |
| A61K 9/00 | (2006.01) | |
| A61K 47/18 | (2017.01) | |
| A61K 9/06 | (2006.01) | |
| A61K 8/04 | (2006.01) | |
| A61K 8/06 | (2006.01) | |

(52) U.S. Cl.
CPC .............. *A61K 8/63* (2013.01); *A61K 8/042* (2013.01); *A61K 8/06* (2013.01); *A61K 9/0014* (2013.01); *A61K 9/06* (2013.01); *A61K 31/566* (2013.01); *A61K 47/183* (2013.01); *A61Q 19/00* (2013.01); *A61Q 19/06* (2013.01); *A61K 2800/75* (2013.01)

(58) Field of Classification Search
CPC .................................. A61K 8/63; A61K 31/56
USPC .......................................................... 514/178
See application file for complete search history.

(56) References Cited

U.S. PATENT DOCUMENTS

| | | | | |
|---|---|---|---|---|
| 4,177,267 A | * | 12/1979 | Herschler | ................ A61K 8/46 514/169 |
| 4,235,893 A | | 11/1980 | Brodie et al. | |
| 5,807,849 A | * | 9/1998 | Labrie | .................. A61K 31/565 514/178 |
| 6,465,446 B1 | * | 10/2002 | Dykstra | ................. A61K 31/56 514/169 |
| 6,586,417 B1 | * | 7/2003 | Abraham | ............... A61K 31/56 514/178 |
| 2003/0199487 A1 | | 10/2003 | Abraham | |
| 2006/0178352 A1 | * | 8/2006 | El-Alfy | .................... A61K 8/63 514/177 |

FOREIGN PATENT DOCUMENTS

| | | |
|---|---|---|
| DE | 696 09 868 T2 | 3/2001 |
| WO | 97/10255 A1 | 3/1997 |
| WO | WO 2007131736 A2 * 11/2007 ........... A61K 31/568 |

OTHER PUBLICATIONS

International Search Report of PCT/DE2014/100366, dated Feb. 11, 2015.
German Office Action in DE 10 2013 111 391.5, dated May 23, 2014, with English translation of relevant parts.

* cited by examiner

*Primary Examiner* — Craig D Ricci
*Assistant Examiner* — Janet L. Coppins
(74) *Attorney, Agent, or Firm* — Collard & Roe, P.C.

(57) ABSTRACT

The invention relates to the use of a steroid-3-carboxylic acid ester, a steroid-4 carboxylic acid ester or a steroid-17 carboxylic acid ester of a steroid, selected from the group of androstanones, androst-4-ene-diones, androst-5-ene-diones, dehydroepiandrosterones, androstenetriones or testosterones, with an acyl group of the carboxylic acid ester

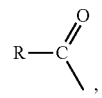

where R is selected from alkyl with at least two carbon atoms or cycloalkyl, or with the use of a compound containing these steroid carboxylic acid esters for local topical application for cosmetic or dermatological purposes. Moreover, this invention also relates to steroid carboxylic acid esters and their compounds used for local topical application.

9 Claims, No Drawings

STEROID CARBOXYLIC ACID ESTERS, COMPOSITIONS CONTAINING STEROID CARBOXYLIC ACID ESTERS, AND USE OF SAID COMPOSITIONS IN LOCAL TOPICAL APPLICATIONS FOR COSMETIC OR DERMATOLOGICAL PURPOSES

CROSS REFERENCE TO RELATED APPLICATIONS

This application is the National Stage of PCT/DE2014/100366 filed on Oct. 15, 2014, which claims priority under 35 U.S.C. § 119 of German Application No. 10 2013 111 391.5 filed on Oct. 15, 2013, the disclosure of which is incorporated by reference. The international application under PCT article 21(2) was not published in English.

SCOPE OF THE INVENTION

This invention relates to the use of a steroid carboxylic acid ester or a compound containing this carboxylic acid ester for local topical application for cosmetic or dermatological purposes. The invention also relates to the use of a steroid carboxylic acid ester or a compound containing this carboxylic acid ester for local topical application for cosmetic or dermatological purposes for the reduction of cellulite, general skin firming, the reduction of stretch marks, a reduction in the size of sears both before and after their formation, the lessening of allergy-related skin irritations or irritations caused by insect bites, ultraviolet radiation or X-rays and general itchiness of the skin. Moreover, this invention also relates to steroid carboxylic acid esters and their compounds used for local topical application.

PRIOR ART

It is known that certain steroid hormones and their metabolites can be used for cosmetic purposes due to their positive effects on the body. Oestrogens, for example, increase the thickness and elasticity of the skin in postmenopausal women when administered both systemically and topically. The increase in thickness is the result of improved hydration and an increase in the collagen concentration in the skin. The main oestrogen receptor in the skin is ERbeta. The topical application of formulations containing oestrogen positively influences the appearance of the skin and its characteristics, but results in systemic and adverse effects due to the high sensitivity of the receptor to oestradiol.

WO 97/10255 A1 relates to certain steroid carboxylic acid esters and their use to regulate skin atrophy and other skin conditions, as well as to the corresponding cosmetic and pharmaceutical preparations.

U.S. Pat. No. 4,235,893 A discloses a method to inhibit the biosynthesis of oestrogen and the use of certain 4-O-n-alkanoyl-androstene-3,17-diones, in which the corresponding acetate, n-heptanoate and n-dodecanoate are named among others.

U.S. Pat. No. 6,586,417 B1 describes the use of certain carboxylic acid esters of 4-hydroxy-androstene-3,17-dione for regulation of the athletic function in humans.

PURPOSE OF THE INVENTION

It is therefore the purpose of the invention to reduce undesirable steroid effects during local topical application for cosmetic or dermatological purposes, while increasing the specificity of the effect on certain skin cells.

DISCLOSURE OF THE INVENTION

The purpose is achieved by the use of a steroid-3-carboxylic acid ester, a steroid-4 carboxylic acid ester or a steroid-17 carboxylic acid ester of a steroid, selected from the group of androstanones, androst-4-ene-diones, androst-5-ene-diones, dehydroepiandrosterones, androstenetriones or testosterones, with an acyl group of the carboxylic acid ester

where R is selected from alkyl with at least two carbon atoms or cycloalkyl, or with the use of a compound containing these steroid carboxylic acid esters for local topical application for cosmetic or dermatological purposes.

This invention is based on the observation that, during the use of certain steroid carboxylic acid esters or a compound containing these for local topical application to the skin, the steroid carboxylic acid esters only have an effect on certain skin cells but not on others, unlike steroids with free hydroxyl groups.

During topical application, the steroid carboxylic acid esters at first rapidly penetrate into the stratum corneum (horny layer) of the epidermis. From this layer, the steroid carboxylic acid esters reach the deeper-lying keratinocyte layers of the epidermis and the fibroblasts of the dermis. It was found that steroid-3-carboxylic acid esters, steroid-4 carboxylic acid esters or steroid-17 carboxylic acid esters of a steroid, selected from the group of androstanones, androst-4-ene-diones, androst-5-ene-diones, dehydroepiandrosterones, androstenetriones or testosterones, with an acyl group of the carboxylic acid ester

where R is selected from alkyl with at feast two carbon atoms or cycloalkyl, have no biological effect on human skin. A biological effect only develops following the hydrolysis of the steroid carboxylic acid ester into the free, hydroxylated steroid and carboxylic acid.

The hydrolysis of the steroid carboxylic acid ester takes place in the keratinocytes. The enzyme that catalyses the hydrolysis of the steroid carboxylic acid ester is human carboxylesterase 2 (hCES2). The part of the steroid carboxylic acid ester that is not hydrolysed in the keratinocyte layer and penetrates into the dermis remains ineffective, as esterase is almost entirely found in the epidermis. The part of the steroid carboxylic acid ester that is not hydrolysed in the keratinocyte layer and penetrates into the dermis and thus into the fibroblasts remains ineffective. This means that a very specific effect of steroids can be released in the keratinocytes in a targeted manner, while on the other hand undesirable effects on other cells, such as fibroblasts, can be avoided.

A further advantage of steroid carboxylic acid esters is that they penetrate more rapidly into the stratum corneum and the stratum lucidum below than the corresponding unesterified steroids. Esterification of the hydroxyl groups of steroids with carboxylic acids reduces their solubility in water. When the steroid carboxylic acid esters are applied to the skin, they dissolve better in the lipids of the stratum corneum and the stratum lucidum than the unesterified steroid. The stratum corneum and stratum lucidum adjoin the stratum granulosum which, like the lower-lying layers of the epidermis—the stratum spinosum and the stratum basale—mainly consists of keratinocytes. The intercellular fluid flows around these cells. As the steroid carboxylic acid esters are more hydrophobic, they subsequently penetrate more slowly into the keratinocyte layer, which can be regarded as a watery environment. The mostly water-insoluble steroid carboxylic add esters only move from the stratum corneum into the stratum basale after some time, so that the combination of relatively easy penetration into the lipids between the horny cells and the slowed-down transfer into the intercellular fluid results in an enrichment of the steroid carboxylic acid esters in the stratum corneum (stratum corneum reservoir). This reservoir constantly yet gradually releases the stored steroid carboxylic acid esters. This results in a slower flooding of the keratinocytes with steroids following topical application to the skin when steroid carboxylic acid esters are used instead of steroids with free hydroxyl groups such as oestradiol or testosterone. These have a longer retention time in the skin than the free hydroxyl steroids. This results in a reservoir effect, which means that the steroid carboxylic acid esters are continuously released into the epidermis. Consequently, the concentration peak of the substances in the keratinocyte layer is also lower and takes place later than for hydroxylated, unesterified steroids.

A further object of the invention is the use of a steroid-3-carboxylic acid ester, a steroid-4 carboxylic acid ester or a steroid-17 carboxylic acid ester of a steroid, selected from the group of androstanones, the androst-4-ene-diones, the androst-5-ene-diones, the dehydroepiandrosterones, the androstenetriones or the testosterones, with an acyl group of the carboxylic acid ester

where R is selected from alkyl with at least two carbon atoms or cycloalkyl, or the use of a compound containing these steroid carboxylic acid esters, for local topical application for cosmetic and dermatological purposes for the reduction of cellulite, for general skin firming, the reduction of stretch marks, a reduction in the size of scars both before and after their formation, the lessening of allergy-related skin irritations or irritations caused by insect bites, ultraviolet radiation or X-rays and general itchiness of the skin.

When using a steroid carboxylic acid ester for topical application to the skin, it was observed that an improvement in the reduction of cellulite, improved general skin firming, improved reduction of stretch marks, improved reduction in the size of scars both before and after their formation, improved lessening of allergy-related skin irritations or irritations caused by insect bites, ultraviolet radiation or X-rays and general itchiness of the skin occurred in comparison with unesterified steroids.

Collagen synthesis in the dermis takes place in the fibroblasts. These cells contain the enzyme aromatase. This enzyme plays a major role in oestrogen synthesis of the skin. The oestrogens bind with the oestrogen receptor beta (ER-beta). This results in increased collagen synthesis in the fibroblasts. It is known that there is a positive correlation between the aromatase activity in the fibroblasts and the reduction of cellulite, general skin firming, a reduction of stretch marks and a reduction in the size of scars both before and after their formation. It was unexpectedly found that allergy-related skin irritations or irritations caused by insect bites, ultraviolet radiation or X-rays and general itchiness of the skin can be very favourably influenced by topical application.

Many steroids from the group of androstanones, androst-4-ene-diones, androst-5-ene-diones, dehydroepiandrosterones, androstenetriones or testosterones are aromatase inhibitors. When these steroids are used for topical application to the skin, they have a detrimental effect on oestrogen synthesis.

However, a large number of metabolic products are created from the aromatase inhibitors in the keratinocytes which, unlike their precursors, no longer act as aromatase inhibitors and which also promote collagen synthesis in the fibroblasts, as they now bind to the oestrogen receptor beta (ERbeta) of the fibroblasts in the same way as oestrogens. Thus the aromatase inhibitors result in high concentrations of ligands for the oestrogen receptor beta in the keratinocytes. These metabolic products of the keratinocytes act paracrinally on the collagen synthesis of the fibroblasts. The unesterified steroids from the group of androstanones, androst-4-ene-diones, androst-5-ene-diones, dehydroepiandrosterones, androstenetriones or testosterones thus have both positive and negative effects.

By contrast, the use of steroid carboxylic acid esters makes it possible to avoid the undesirable effect of reducing the positive effect of the steroids. This improves the positive effect of the steroids on the oestrogen receptor beta and thus the effects associated with the activation of this receptor regarding the reduction of cellulite, general skin firming, a reduction in stretch marks, a reduction in the size of scars both before and after their formation, a lessening of allergy-related skin irritations or irritations caused by insect bites, ultraviolet radiation or X-rays and general itchiness of the skin.

According to an advantageous embodiment of the invention, the steroid carboxylic acid ester is a derivative of 4-hydroxyandrostenedione. The steroid-4-carboxylic acid ester of the androstenedione is split in the keratinocytes. Moreover, 4-hydroxyandrostenedione acts as a significant metabolite in the keratinocytes, resulting in a compound that no longer has the keto group of the androstenedione at C3, but a hydroxyl group. In addition, this compound no longer acts as a C4=C5 double bond. Of the hydroxyl groups at C3, 70% are in the beta position. This results in the molecule 3beta, 4beta-dihydroxy-5alpha-androstan-17-on. Furthermore, the keto group is reduced by C-17 in the keratinocytes, resulting in a triol. This binds very well with the oestrogen receptor beta (ERbeta). Steroid carboxylic acid esters of the 4-hydroxyandrostenedione are preferred, as they result in a very efficient reduction of cellulite.

According to a further advantageous embodiment of the invention, the acyl group of the carboxylic acid ester is free of polar substitutes. The radical R, which has been selected from alkyl with at least two carbon atoms or cycloalkyl, contains no polar substitutes. The lower solubility of the steroid carboxylic acid ester in water in comparison with the unesterified steroids is significant for the formation of a stratum corneum reservoir. Hydroxyl groups or other polar substitutes from the acyl group have a negative effect on the formation of the reservoir effect, as the radical R would obtain a more hydrophilic character through the polar substitutes. The influences of a polar and thus hydrophilic substitute would necessarily have to be compensated for by additional hydrophobic units. Hydroxyl groups and other polar substitutes of the acyl group of the carboxylic acid ester, such as amino groups or carboxyl groups, are thus not desirable.

According to a further advantageous embodiment of the invention, the alkyl radical of the acyl group is either unbranched or branched. If the alkyl radical is thus selected from: ethyl, propyl, isopropyl, butyl, sec-butyl (1-methylpropyl), isobutyl (2-methylpropyl), tert-butyl (1,1-dimethylethyl), pentyl, hexyl and structural isomers of pentyl or hexyl, a very good rate of hydrolysis of the steroid carboxylic acid esters by the hCES2 of the keratinocytes may be observed.

According to a further advantageous embodiment of the invention, the cycloalkyl radical is selected from, cyclopropane, cyclopentane or cyclohexane. These cycloalkyls are split off from the corresponding steroid carboxylic acid esters by the hCES2 of the keratinocytes at a very good hydrolysis rate.

According to a further advantageous embodiment of the invention, the steroid carboxylic acid ester is 4-O-propionyl-androstene-3,17-dione, 4-O-butyryl-androstene-3,17-dione, 4-O-valeryl-androstene-3,17-dione, 4-O-caproyl-androstene-3,17-dione or 4-O-enantyl-androstene-3,17-dione. The steroid carboxylic acid esters have an excellent hydrolysis rate due to the hCES2 of the keratinocytes and also result in the distinct activation of the oestrogen receptor beta (ER-beta) via the metabolites formed in the keratinocytes. Especially when using 4-O-propionyl-androst-4-ene-3,17-dione, the results achieved with regard to the reduction of cellulite, general skin firming, a reduction in stretch marks, a reduction in the size of scars both before and after their formation, a lessening of allergy-related skin irritations or irritations caused by insect bites, ultraviolet radiation or X-rays and general itchiness of the skin were particularly good.

According to a further advantageous embodiment of the invention, the steroid carboxylic acid ester forms part of a compound in a ratio of 0.001 to 10% by weight of the total volume of the compound. The content of the active substance is adapted to the respective application in this case. Preferably, suitable active substance contents of steroid carboxylic acid esters in the compound as a whole range from 0.001 to 5% by weight and particularly from 0.3 to 2% by weight.

According to a further advantageous embodiment of the invention, the steroid carboxylic acid ester forms part of a compound formulated as an ointment, cream, gel, oil, emulsion or lotion. This facilitates topical application. The compound thus includes additives commonly used for the respective formulation as an ointment, cream, gel, oil, emulsion or lotion. Any other additives may be used in the amounts normally added to the respective formulations.

A further object of the invention is 4-O-propionyl-androst-4-ene-3,17-dione with the formula

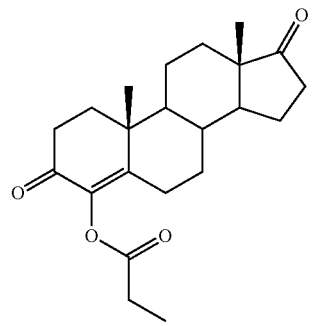

for use as a local topical application for cosmetic or dermatological purposes.

It has been demonstrated that topical application of 4-O-propionyl-androst-4-ene-3,17-dione to the skin resulted in an improvement in the reduction of cellulite, improved general skin firming, improved reduction of stretch marks, improved reduction in the size of scars both before and after their formation, improved lessening of allergy-related skin irritations or irritations caused by insect bites, ultraviolet radiation or X-rays and general itchiness of the skin.

A further object of the invention is a compound used for local topical application for cosmetic or dermatological purposes that contains at least one steroid-3-carboxylic acid ester, one steroid-4-carboxylic acid ester or one steroid-17-carboxylic acid ester of a steroid selected from the group of androstanones, androst-4-ene-diones, androst-5-ene-diones, dehydroepiandrosterones, androstenetriones or testosterones, with one acyl group of the carboxylic acid ester

where R is selected from alkyl with at least two carbon atoms or cycloalkyl, in a formulation as an ointment, cream, gel, oil, emulsion or lotion.

The compound for local topical application is particularly suitable for cosmetic and dermatological purposes for the reduction of cellulite, for general skin firming, the reduction of stretch marks, a reduction in the size of scars both before and after their formation, the lessening of allergy-related skin irritations or irritations caused by insect bites, ultraviolet radiation or X-rays and general itchiness of the skin, it has been demonstrated that topical application of the compound to the skin resulted in an improvement in the reduction of cellulite, improved general skin firming, improved reduction of stretch marks, improved reduction in the size of scars both before and after their formation, improved lessening of allergy-related skin irritations or irritations caused by insect bites, ultraviolet radiation or X-rays and general itchiness of the skin.

According to an advantageous embodiment of the compound, the steroid carboxylic acid ester is a derivative of 4-hydroxyandrostenedione. Preferably the radical R of the acyl group of the carboxylic acid ester is an alkyl radical with at least two carbon atoms and either unbranched or branched. It is advantageous to select the alkyl radical from ethyl, propyl, isopropyl, butyl, sec-butyl (1-methylpropyl), isobutyl (2-methylpropyl), tert-butyl (1,1-dimethylethyl), pentyl, hexyl and structural isomers of pentyl or hexyl. Another advantageous embodiment provides for the radical R of the acyl group to be a cycloalkyl radical and for the cycloalkyl radical to be selected from cyclopropane, cyclopentane or cyclohexane.

According to a further advantageous embodiment of the compound, the acyl group of the carboxylic acid ester is free of polar substitutes.

According to a further advantageous embodiment of the compound, the steroid carboxylic acid ester is 4-O-propionyl-androstene-3,17-dione, 4-O-butyryl-androstene-3,17-dione, 4-O-valeryl-androstene-3,17-dione, 4-O-caproyl-androstene-3,17-dione or 4-O-enantyl-androstene-3,17-dione. The steroid carboxylic acid esters have an excellent hydrolysis rate due to the hCES2 of the keratinocytes and also result in the distinct activation of the oestrogen receptor beta (ERbeta) via the metabolites formed in the keratinocytes.

According to a further advantageous embodiment of the compound, the steroid carboxylic acid ester forms part of the compound in a ratio of 0.001 to 10% by weight of the total volume of the compound.

According to a further advantageous embodiment of the compound, the steroid carboxylic acid ester forms part of the compound in a ratio of 0.001 to 5% by weight of the total volume of the compound.

The compound in accordance with the invention may contain cosmetic additives commonly used for corresponding formulation as an ointment, cream, gel, oil, emulsion or lotion, such as fats, oils, waxes, alcohols, polyols, polymers, anti-foaming agents, colourants, pigments, thickening agents, surfactants, emulsifiers, plasticisers, preservatives, anti-oxidants, buffer substances, aromatic substances and/or fragrances in the amounts usually used for the various formulations.

The following examples are intended to explain the invention, but not to restrict it. Where not otherwise stated, the numbers refer to a percentage by weight.

EXAMPLE 1

Formulation and Production of an Emulsion in Accordance with the Invention

| Phase | INCI name | % by weight |
|---|---|---|
| A | Aqua/water | 77.9968 |
|   | Disodium EDTA | 0.1000 |
|   | Panthenol | 0.1000 |
|   | Sorbitol | 0.4000 |
|   | Xanthan | 0.5000 |
|   | Glycerin | 5.0000 |
|   | Butylene glycol | 1.6000 |
|   | Ethylhexylglycerin | 0.4000 |
| B | Cetyl alcohol | 2.0000 |
|   | Dimethicone | 1.1000 |
|   | Potassium cetyl phosphate | 0.7000 |
|   | C20-22 alkyl phosphate | 1.8000 |
|   | C20-22 alkyl alcohols | 1.5000 |
|   | Caprylic/capric triglyceride | 3.0000 |
| C | Propylene glycol | 1.0000 |
|   | Chlorphenesin | 0.2000 |
|   | Phenoxyethanol | 0.7000 |
| D | Jojoba oil | 0.5000 |
|   | Tocopheryl acetate | 0.0500 |
|   | Lecithin | 0.0210 |
|   | Tocopherol | 0.0045 |

-continued

| Phase | INCI name | % by weight |
|---|---|---|
|   | Ascorbyl palmitate | 0.0030 |
|   | Citric acid | 0.0015 |
|   | Ascorbyl tetraisopalmitate | 0.1000 |
| E | Phytanic acid | 0.0800 |
|   | Lactic acid | 0.4500 |
|   | Sodium hydroxide | 0.2400 |
| F | 4-O-propionyl-androst-4-ene-3,17-dione | 0.2000 |
|   | Aromatic substances/fragrance | 0.2500 |
| H | Caramel | 0.0032 |

Preparation:

The ingredients for Phase A are mixed and heated to 70 to 75° C. white stirring. The ingredients for Phase 8 are mixed, heated to 70 to 75° C. and added to Phase A while stirring. The mixture of A and B is cooled to 50° C. while stirring. Phase C is added, while continuing to stir. The ingredients for Phase D are mixed and added to the Phase A+B+C while stirring. The ingredients for Phase E are mixed and added to the Phase A+B+C+D while stirring. Phase F is added to the A+B+C+D+E Phase while stirring at a maximum temperature of 30 to 35° C. Phase G is added to the A+B+C+D+E+F Phase while stirring at a maximum temperature of 25° C. Phase H is added to the A+B+C+D+E+F+G Phase while stirring at a maximum temperature of 25° C. All steps of this preparation process can be carried out in a vacuum mixer to obtain particularly homogeneous compounds that do not contain air bubbles.

EXAMPLE 2

Formulation and Production of a Cream in Accordance with the Invention

| Phase | INCI name | % by weight |
|---|---|---|
| A | Aqua/water | 78.9830 |
|   | Disodium EDTA | 0.1500 |
|   | Sorbitol | 0.4000 |
|   | Glycerin | 2.0000 |
|   | Ethylhexylglycerin | 0.4000 |
|   | Xanthan | 0.3000 |
| B | Cetearyl alcohol | 1.9000 |
|   | Caprylic/capric triglyceride | 1.7000 |
|   | Cetearyl glucoside | 0.7900 |
|   | Glyceryl stearate | 0.9000 |
|   | Ethylhexyl palmitate | 1.6000 |
|   | Cetyl palmitate | 1.6000 |
|   | Dicaprylyl carbonate | 2.0000 |
|   | Shea butter | 0.5000 |
|   | White beeswax-Cera alba | 0.3000 |
|   | Sodium polyacrylate | 1.0000 |
|   | PEG-100 stearate | 0.9000 |
|   | Hydrogenated polydecene | 0.8000 |
|   | Trideceth-6 | 0.1600 |
| C | Chlorphenesin | 0.2000 |
|   | Phenoxyethanol | 0.7000 |
| D | Jojoba oil | 0.5000 |
|   | Tocopheryl acetate | 0.1000 |
|   | Lecithin | 0.0350 |
|   | Tocopherol | 0.0075 |
|   | Ascorbyl palmitate | 0.0050 |
|   | Citric acid | 0.0025 |
| E | Lactic acid | 0.9000 |
|   | Sodium hydroxide | 0.6000 |
| F | Phytanic acid | 0.2000 |
| G | Ascorbyl tetraisopalmitate | 0.1000 |
| H | 4-O-propionyl-androst-4-ene-3,17-dione | 0.1000 |
| I | Aromatic substances/fragrance | 0.1670 |

Preparation:

The ingredients for Phase A are mixed and heated to 70 to 75° C. while stirring. The ingredients for Phase B are mixed, heated to 70 to 75° C. and added to Phase A while stirring. The mixture of A and B is cooled to 50° C. while stirring. Phase C is added, while continuing to stir. The ingredients for Phase D are mixed and added to the Phase A+B+C while stirring. The ingredients for Phase E are mixed and added to the Phase A+B+C+D while stirring. Phase F is added to the A+B+C+D+E Phase while stirring at a maximum temperature of 35 to 4° C. Phase G is added to the A+B+C+D+E+F Phase while stirring at a maximum temperature of 35 to 40° C. Phase H is added to the A+B+C+D+E+F+G Phase while stirring at a maximum temperature of 30 to 35° C. Phase I is added to the A+B+C+D+E+F+G+H Phase while stirring at a maximum temperature of 25° C. All steps of this preparation process can be carried out in a vacuum mixer to obtain particularly homogeneous compounds that do not contain air bubbles.

EXAMPLE 3

Formulation of Another Cream in Accordance with the Invention

| Description | % by weight |
| --- | --- |
| Aqua/water | 56.8 |
| Propylene glycol | 25.0 |
| Isopropyl myristate | 6.0 |
| Cetearyl stearyl alcohol | 6.0 |
| Stearyl alcohol | 2.0 |
| Polysorbate 80 (polyoxyethylene(20)-sorbitan-monooleate) | 2.0 |
| Sorbitan monostearate | 1.0 |
| Glycerol monostearate | 1.0 |
| 4-O-propionyl-androst-4-ene-3,17-dione | 0.1 |
| Hyaluronic acid | 0.1 |

EXAMPLE 4

Formulation of Another Cream in Accordance with the Invention

| INCI name | % by weight |
| --- | --- |
| Aqua/water | 62.85 |
| Jojoba oil | 6.05 |
| Cocoglycerides | 5.95 |
| Dimethyl isosorbide | 5.00 |
| Glycerin | 4.20 |
| Sorbitol | 4.00 |
| Shea butter | 3.00 |
| Polyglyceryl-3-methylglucose distearate | 3.00 |
| Cetearyl alcohol | 2.20 |
| Yellow beeswax-Cera flava | 1.00 |
| Tocopheryl acetate | 1.00 |
| Polysol AC: | 0.70 |
| Phenoxyethanol | |
| Dehydroacetic acid | |
| Sorbic acid | |
| Benzoic acid | |
| Lactic acid | |
| 4-O-propionyl-androst-4-ene-dione | 0.09 |
| Xanthan | 0.25 |
| Aromatic substances/fragrance | 0.20 |
| Tetrasodium iminodisuccinate | 0.10 |
| Ethylhexylglycerin | 0.10 |
| Lactic acid, 80% | 0.10 |
| Ascorbyl tetraisopalmitate | 0.10 |
| Phytanic acid | 0.05 |
| Controx VP: | 0.04 |
| Lecithin | |
| Ascorbyl palmitate | |
| Hydrogenated palm glycerides citrate | |
| Tocopherol | |
| Sodium hydroxide | 0.02 |

EXAMPLE 5

Formulation of an Oil-Based Gel in Accordance with the Invention

| Description | % by weight |
| --- | --- |
| Olive fruit oil | 45.37 |
| Caprylic/capric triglycerides | 31.40 |
| Glycerin | 15.00 |
| Polyglyceryl-5-oleate | 6.00 |
| Aqua/water | 1.88 |
| 4-O-propionyl-androst-4-ene-3,17-dione | 0.15 |
| Tocopherol, sunflower oil | 0.20 |

Results of a Clinical Study With a Cream Containing 4-O-propionyl-androst-4-ene-3,17-dione—Efficacy in the Treatment of Cellulite In a study carried out by an independent dermatological institute (Dermatest, Münster), a cream containing 0.10% 4-O-propionyl-androst-4-ene-3,17-dione was tested on female test subjects for efficacy and tolerability.

Trial Protocol:

The trial involved 20 female test subjects (aged between 32 and 58 years, average age 45.1 years). One test subject prematurely terminated the trial after 8 weeks due to pregnancy; one new test subject (21st test subject) was incorporated at the beginning of the ninth week.

The cream was applied once a day over a period of 12 weeks. The efficacy and tolerability (skin elasticity, thigh circumference, width and height of the protruding lobules) were evaluated after 4, 3 and 12 weeks.

Efficacy:

Skin Elasticity

The skin elasticity was measured with a Cutometer. The skin elasticity increased in 100% of the test subjects. After 4 weeks the average increase was 14%, whereas after 12 weeks the average increase was 22.42%, 95% of the test subjects experienced a subjective improvement in skin elasticity.

Surface Area of the Fat Lobules

A surprising effect was observed with regard to the size of the protruding fat lobules that are responsible for the characteristic appearance of cellulite. The surface area corresponding to their size was measured during an ultrasound examination.

The surface area of the fat lobules was reduced in 100% of the test subjects. After 4 weeks the surface area of the fat lobules had been reduced by an average of 23.24%, after 8 weeks the average reduction in the surface area was 34.51% and after 12 weeks the average reduction in the surface area of the fat lobules was 44.06%.

According to a statement made by the independent research institute, such an effect has thus far not been observed in any competing product.

Thigh Circumference

The thigh circumference was reduced in 100% of the test subjects. After 4 weeks, the thigh circumference of the test subjects had been reduced by an average of 0.6 cm or 1.04%, whereas after 12 weeks the average reduction in thigh circumference was 1.87 cm or 3.25%.

Further Options for Use in Cosmetic Products a) Stretch marks/striae
b) Wrinkles (anti-ageing)
c) Skin care following radiation therapy (oncological care)

Each of the product ideas for the treatment of stretch marks/striae and scar care is the result of repeated positive observations made during the use of the cream containing 4-O-propionyl-androst-4-ene-3,17-dione; in all three applications the cream containing 4-O-propionyl-androst-4-ene-3,17-dione yielded clearly better results than products already on the market.

All features of the invention can be material to the invention both individually and in any combination. Further advantages and advantageous embodiments of the invention are presented in the claims.

The invention claimed is:

1. A method of improving the condition of the skin in a subject in need thereof, comprising topically applying locally for cosmetic or dermatological purposes to a subject, wherein the cosmetic or dermatological purposes comprise reduction of cellulite, general skin firming, reduction of stretch marks, prevention of scar formation, reduction in the size of scars after their formation, lessening of allergy-related skin irritations or irritations caused by insect bites, ultraviolet radiation, or X-rays and general itchiness of the skin, a composition comprising a steroid-4 carboxylic acid ester that is a derivative of 4-hydroxyandrostenedione according to the following structure:

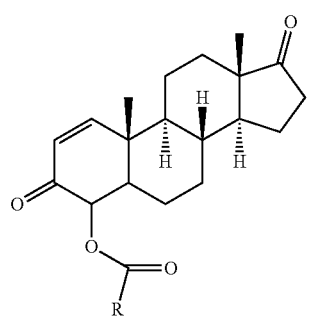

where R is selected from alkyl with at least two carbon atoms or cycloalkyl, wherein the steroid-4 carboxylic acid ester is contained in the composition in an amount of 0.001 to 10% by weight based on the total amount of the composition.

2. The method in accordance with claim 1, wherein the acyl group of the steroid-4 carboxylic acid ester is free of polar substitutes.

3. The method in accordance with claim 1, wherein the radical R of the acyl group is an alkyl radical with at least two carbon atoms and wherein the alkyl radical is either unbranched or branched.

4. The method in accordance with claim 1, wherein the radical R of the acyl group is an alkyl radical with at least two carbon atoms and wherein the alkyl radical has been selected from ethyl, propyl, isopropyl, butyl, sec-butyl (1-methylpropyl), isobutyl (2-methylpropyl), tert-butyl (1,1-dimethylethyl), pentyl, hexyl and structural isomers of pentyl or hexyl.

5. The method in accordance with claim 1, wherein the radical R of the acyl group is a cycloalkyl radical and wherein the cycloalkyl radical has been selected from cyclopropane, cyclopentane or cyclohexane.

6. The method in accordance with claim 1, wherein the steroid-4 carboxylic acid ester is 4-O-propionyl-androstene-3,17-dione, 4-O-butyryl-androstene-3,17-dione, 4-O-valeryl-androstene-3,17-dione, 4-O-caproyl-androstene-3,17-dione or 4-O-enantyl-androstene-3,17-dione.

7. The method in accordance with claim 1, wherein the steroid-4 carboxylic acid ester is 4-O-propionyl-androst-4-ene-3,17-dione with the formula

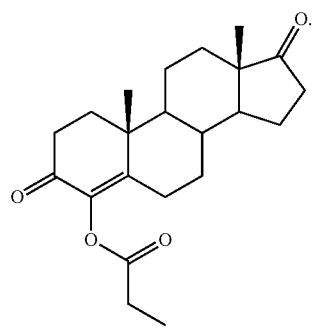 [SMILES: CCC(=O)OC1=C2CCC3C(CC[C@]4(C)C(=O)CCC34)[C@@]2(C)CCC1=O]

8. The method in accordance with claim 1, wherein the steroid-4 carboxylic acid ester is contained in the composition in an amount of 0.001 to 5% by weight based on the total amount of the composition.

9. A method of improving the condition of the skin in a subject in need thereof, comprising topically applying locally for cosmetic or dermatological purposes to a subject, wherein the cosmetic or dermatological purposes comprise reduction of cellulite, general skin firming, reduction of stretch marks, prevention of scar formation, reduction in the size of scars after their formation, lessening of allergy-related skin irritations or irritations caused by insect bites, ultraviolet radiation, or X-rays and general itchiness of the skin, a composition comprising a steroid-4 carboxylic acid ester that is a derivative of 4-hydroxyandrostenedione according to the following structure:

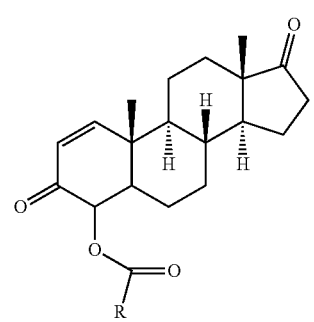

where R is selected from alkyl with at least two carbon atoms or cycloalkyl, and wherein the steroid-4 carboxylic acid ester is contained in the composition formulated as an ointment, cream, gel, oil, emulsion or lotion.

* * * * *